United States Patent [19]

Aberg

[11] Patent Number: 4,753,792
[45] Date of Patent: Jun. 28, 1988

[54] TOOTH CLEANING TABLET

[76] Inventor: Torwald Aberg, Gotgatan 93, 11662 Stockholm, Sweden

[21] Appl. No.: 928,571

[22] Filed: Nov. 10, 1986

Related U.S. Application Data

[63] Continuation of Ser. No. 765,158, Aug. 13, 1985, abandoned.

[30] Foreign Application Priority Data

Aug. 21, 1984 [GB] United Kingdom ............... 8421226

[51] Int. Cl.$^4$ .................... A61K 9/46; A61K 9/20; A61K 7/16; A61K 7/18
[52] U.S. Cl. ......................... 424/44; 424/49; 424/52
[58] Field of Search ............ 424/44, 49, 58, 52

[56] References Cited

U.S. PATENT DOCUMENTS

| | | | |
|---|---|---|---|
| 1,262,888 | 4/1918 | Westlake | 424/44 |
| 1,411,681 | 4/1922 | Burlew | 424/49 |
| 2,778,045 | 1/1957 | Bly et al. | 424/49 |
| 3,116,208 | 12/1963 | Emond | 424/56 |
| 3,151,028 | 9/1964 | Hay et al. | 424/55 |
| 3,431,339 | 3/1969 | Gyarmathy et al. | 424/57 |
| 3,962,417 | 6/1976 | Howell | 424/44 |
| 3,997,658 | 12/1976 | Block et al. | 424/7.1 |
| 4,344,931 | 8/1982 | Aguilar | 424/49 |
| 4,411,885 | 10/1983 | Barels et al. | 424/49 |
| 4,427,116 | 1/1984 | Brown | 424/49 |
| 4,432,114 | 2/1984 | Goudsmit | 424/49 |

FOREIGN PATENT DOCUMENTS

| | | |
|---|---|---|
| 1202629 | 8/1970 | United Kingdom . |
| 1259342 | 1/1972 | United Kingdom . |
| 1452809 | 10/1976 | United Kingdom . |
| 2008948 | 6/1979 | United Kingdom . |
| 1548377 | 7/1979 | United Kingdom . |
| 1561362 | 2/1980 | United Kingdom . |
| 2050824 | 1/1981 | United Kingdom . |
| 2071493 | 9/1981 | United Kingdom . |

Primary Examiner—Shep K. Rose
Attorney, Agent, or Firm—F. Eugene Davis, IV; Mark P. Stone

[57] ABSTRACT

A tooth cleaning tablet which is self-foaming and self-cleansing on chewing and which includes a self-foaming effervescent couple composition which enables the tablet readily to form a foam on chewing without the need for agitation with a toothbrush and also without the need to suck air into the mouth, the self-foaming effervescent couple composition comprising a carboxylic acid, an alkali metal carbonate salt, a wetting agent such as sodium lauryl sulphate, and a swelling agent such as zanthan gum.

21 Claims, No Drawings

TOOTH CLEANING TABLET

This application is a continuation of application Ser. No. 765,158 filed Aug. 13, 1985 now abandoned.

This invention relates to a tooth cleaning tablet. The world wide practice of tooth cleaning is usually effected with tooth paste. The tooth paste is sold in tubes of different sizes but there invariably occurs the problem of squeezing the last drop of tooth paste from the tube to avoid wastage. To a lesser extent there also invariably occurs the problem of where and how to squeeze the tube during use in order to ensure the easy dispensation of the tooth paste when there is not much of it left in the tube.

It is an aim of the present invention to obviate or reduce the above mentioned problems.

Accordingly, the present invention provides a tooth cleaning tablet which is self-foaming and self-cleansing on chewing, which tooth cleaning tablet comprises:
(i) a polishing agent,
(ii) a filling agent,
(iii) a taste giving agent,
(iv) a lubricative agent, and
(v) a self-foaming effervescent couple composition which enables the tablet readily to form a foam on chewing without the need for agitation with a toothbrush and also without the need to suck air into the mouth,
the self-foaming effervescent couple composition comprising:
(a) a carboxylic acid,
(b) an alkali metal carbonate salt,
(c) a wetting agent, and
(d) a swelling agent, the self-foaming effervescent couple composition being such that the carboxylic acid, the alkali metal carbonate salt, the wetting agent and the swelling agent are all water soluable and in powder form.

The advantages of the tooth cleaning tablet over tooth paste are legion. For example, packaging of tablets can virtually be changed at will to meet different modes of distribution and different markets. The many and various techniques used for packaging and selling medicinal tablets can be employed for packaging and selling the tooth cleaning tablets. Thus, the tablets can be trapped between two layers of metallic foil and sold in packets in boxes, with for example four or six tablets to a packet. Alternatively, the tablets can be pressed through metallic foil from individual compartments in a plastics base. Still further, the tablets can be placed in loose tubes, or individually wrapped, or wrapped in columns. For travelling purposes, a plurality of the tablets may be provided in a tube that also houses a tooth brush of the type that can be housed in a tube for storage or travel.

The tooth cleaning tablets may be cheaper to produce and package than conventional tooth paste. Storing of the tablets prior to sale may be easier. Portion control and distribution in institutions such as hospitals, prisons and nursery schools becomes easily possible.

The tablets may be easily distributed through vending machines, and this is of obvious benefit to persons using hotels, airlines and shipping lines. Indeed, simply by using different flavours and/or colours, a hotel, airline or shipping line could have its own individual tablets. The tablets could be sold or given away with the compliments of the management. Also, if desired, the tablets could be produced in a colour and/or a shape that was attractive to children to give them an incentive to use the tablets and so clean their teeth.

Usually, the tooth cleaning tablet will be water free.

The tablet is preferably a hard brittle tablet. Such a tablet is crushed as it is chewed in a person's mouth. It is to be appreciated that the tablet need not be brittle and that it could be in another form such as that of a solidified gel.

Preferably, the tablet comprises:
(i) a polishing agent
(ii) a swelling agent
(iii) a foaming agent
(iv) a filling agent
(v) a taste-giving agent
(vi) a wetting agent, and
(vii) a lubricative agent.

The polishing agent may be a phosphate, a carbonate or a polymer.

The phosphate may be a metal phosphate. Typical metal phosphates are sodium metaphosphate, potassium metaphosphate, calcium pyrophosphate, magnesium orthophosphate, trimagnesium phosphate, tricalcium phosphate and dicalcium phosphate.

Typical carbonates are calcium carbonate and sodium bicarbonate.

The swelling agent may be sodiumcarboxymethylcellulose, irish moss, tragacanth gum, accaceia gum, gelatin, an alginic compound, methylcellulose polyvinylpyrrolidon or xanthan gum. The xanthan gum is preferably that sold under the Trade Mark KELTROL.

The alginic compound may be an alginic acid, an alginic salt, or an alginic ester.

The carboxylic acid may be citric, tartaric or malic acid.

The alkali metal carbonate salt may be a sodium carbonate salt such for example as sodium bicarbonate.

The filling agent may be a waxy polyethylene glycol such for example as that known as carbowax 6000 or carbowax 4000.

The filling agent may alternatively be a hexitol component such for example as mannitol or sorbitol.

Still further, the filling agent may be lactose, starch.

The tooth cleaning tablet may include a flowing agent, for example a silicon oxide such as silicon dioxide.

Preferably, the taste-giving agent is at least one compound selected from the group consisting of menthol, peppermint and cyklamate.

The wetting agent may be an oxyethylenoxypropylene polymer, a polyoxyethylensorbitan derivative from a fatty acid, or sodium laurylsulphate. The derivative from the fatty acid may be polyoxyethylensorbitanstearate. A presently preferred anionic wetting agent is the sodium laurylsulphate sold under the trade mark Texapon K12.

The tooth cleaning tablet may also contain an aroma-giving agent, for example peppermint oil or spearmint oil.

The tooth cleaning tablet may also contain a plaque indicating agent.

The lubricative agent may be magnesium stearate. The sodium monofluorophosphate may be used in amounts up to 1% by volume of the tablet.

The tooth cleaning tablet may also contain a sweetening agent. The sweetening agent may be sugar or a sugar based substance. A replacement substance for sugar may advantageously be employed such for example as zylitol.

Embodiments of the invention will now be given with reference to the accompanying Examples.

EXAMPLE 1

A water-free tooth cleaning tablet was produced using methods known in themselves for producing medicinal tablets. The tooth cleaning tablet was produced in moisture-free air and it had the following composition:

| | | |
|---|---|---|
| 0.213 g | Tricalciumphosphate | Polishing agent |
| 0.053 g | Keltrol | Swelling agent |
| 0.08 g | Sodium bicarbonate | Foaming agent |
| 0.032 g | Citric Acid | Foaming agent |
| 0.192 g | Sorbitoleum | Filling agent |
| 0.04 g | Cyklamate | Taste-giving agent |
| 0.010 g | Texapon K12 | Wetting agent |
| 0.005 g | Magnesium Stearate | Lubricative agent |
| 2% | Natural Aroma | Aroma-giving agent |
| 0.625 g | | |

The Natural Aroma was present as 2% by weight. The aroma-giving agent may also be an agent which contributes to the taste of the tooth cleaning tablet.

The produced tooth cleaning tablet was hard and brittle. It was chewed in the mouth for approximately 15 seconds during which time it firstly became crushed and secondly formed a paste. The formation of the paste enabled the person chewing the tablet to stop chewing and to effect a tooth cleaning operation as though using tooth paste. After mouth rinsing, the teeth were found to be at least as satisfactorily cleaned as with conventional tooth paste and some persons found the tablet more pleasant to use than tooth paste.

EXAMPLE 2

A water-free tooth cleaning tablet was produced to have all the ingredients of the tablet of Example 1, and it also had a plaque-indicating agent. On chewing of the tablet to form the paste, the plaque-indicating agent was effective to indicate those areas of the teeth where plaque was present and which thus required special cleaning.

It is to be appreciated that the Examples hereinbefore given have been given for purposes of illustration only and they are not intended to be limiting in any way. Thus, more than one of each of the polishing, swelling, filling, taste-giving, wetting, lubricative and aroma-giving agents listed in Example 1 may be employed if desired.

I claim:

1. A substantially water free non-oil based tooth cleaning and tooth fluoridating tablet forming a self-foaming paste when chewed in the mouth comprising:
   A. less than about 50% by weight of a self foaming effervescent couple composition producing carbon dioxide when placed in the mouth;
   B. greater than about 35% by weight of a substantially insoluble filling and polishing composition; and a foam stabilizing and wetting composition which together form a paste on chewing in the mouth; and,
   C. an effective amount of a fluoride tooth protecting agent.

2. A tooth cleaning tablet according to claim 1 wherein said filling and polishing, and said foam stabilizing and wetting compositions comprise greater than about 50% by weight of said tablet.

3. A tooth cleaning and tooth fluoridating tablet according to claim 2 wherein said self-foaming effervescent couple composition comprises less than about 25% by weight of said tablet.

4. A substantially water free non-oil based tooth cleaning and tooth fluoridating tablet forming a self-foaming paste when chewed in the mouth comprising by weight:
   A. about 65% of a polishing and filling composition;
   B. about 18% of a effervescent couple foam producing composition; and,
   C. an effective amount of a fluoride tooth protecting agent.

5. A tooth cleaning and tooth fluoridating tablet according to claim 4 comprising by weight about 34% polishing agent and about 31% filling agent.

6. A tooth cleaning and tooth fluoridating tablet according to claim 4 comprising about 13% sodium bicarbonate and about 5% acid.

7. A tooth cleaning and tooth fluoridating tablet according to claim 4 and about 8.5% swelling agent.

8. A tooth cleaning and tooth fluoridating tablet according to claim 4 and about 1.5% wetting agent.

9. A tooth cleaning and tooth fluoridating tablet according to claim 5 comprising about 13% sodium bicarbonate and about 5% acid and
   C. about 8.5% swelling agent; and,
   D. about 1.5% wetting agent.

10. A tooth cleaning and tooth fluoridating tablet according to claim 9 and
    E. about 10% lubricating agent.

11. A tooth cleaning and tooth fluoridating tablet according to claim 4 wherein said polishing agent is tricalcium phosphate.

12. A substantially water free non-oil based tooth cleaning tablet forming a self-foaming paste when chewed in the mouth comprising:
    A. self-foaming effervescent couple composition producing carbon dioxide when placed in the mouth;
    B. a substantially insoluble filing and polishing composition which forms a paste on chewing in the mouth; and,
    C. an effective amount of a fluoride tooth protecting agent.

13. A tooth chewing tablet according to claim 12 wherein said self-foaming effervescent couple carbon dioxide producing composition comprises less than about 50% by weight of said tablet.

14. A tooth chewing tablet according to claim 12 wherein said insoluble filing and polishing composition comprises greater than about 35% by weight of said tablet.

15. A tooth chewing tablet according to claim 14 wherein said insoluble filing and polishing composition comprises greater than about 50% by weight of said tablet.

16. A tooth cleaning tablet forming a self-foaming paste when chewed in the mouth comprising by weight:
    A. about 75% polishing and filing agents; and,
    B. about 18% of a self-foaming effervescent couple carbon dioxide producing composition.

17. The tooth cleaning tablet of claim 16 wherein said polishing agent comprises about 34% of the tablet.

18. The tooth cleaning table of claim 17 and said tablet further comprises:
    C. about 8.5% of a swelling agent; and, D. about 1.5% of a wetting agent.

19. The method of tooth cleaning and fluoridating comprising:
   A. placing a tablet according to claim 1 in the mouth;
   B. chewing the tablet to form a self-foaming paste in the mouth;
   C. swishing the paste around and through the interstices between the teeth to mechanically clean the teeth and bring fluoride ions in contact with the tooth surfaces; and
   D. rinsing the mouth of the excess paste.

20. The method of tooth cleaning and fluoridating comprising:
   A. placing a tablet according to claim 4 in the mouth;
   B. chewing the tablet to form a self-foaming paste in the mouth;
   C. swishing the paste around and through the interstices between the teeth to mechanically clean the teeth and bring fluoride ions in contact with the tooth surfaces; and
   D. rinsing the mouth of the excess paste.

21. The method of tooth cleaning and fluoridating comprising:
   A. placing a tablet according to claim 12 in the mouth;
   B. chewing the tablet to form a self-foaming paste in the mouth;
   C. swishing the paste around and through the interstices between the teeth to mechanically clean the teeth and bring fluoride ions in contact with the tooth surfaces; and
   D. rinsing the mouth of the excess paste.

* * * * *